United States Patent [19]

Conti

[11] Patent Number: 4,826,826

[45] Date of Patent: May 2, 1989

[54] METHYLATED CHITOSANS AND THEIR USE FOR THE PREPARATION OF PHARMACEUTICAL COMPOSITIONS

[75] Inventor: Franco Conti, Milan, Italy

[73] Assignee: Establissement Texcontor, Spain

[21] Appl. No.: 55,306

[22] Filed: May 29, 1987

[30] Foreign Application Priority Data

Jun. 16, 1986 [IT] Italy ................................ 20796 A/86

[51] Int. Cl.$^4$ ................. A61K 31/715; A61K 31/735; C08B 37/08; C08L 5/08
[52] U.S. Cl. ..................................... 514/55; 514/839; 514/892; 536/20
[58] Field of Search ......................... 514/55, 892, 839; 536/20

[56] References Cited

U.S. PATENT DOCUMENTS

| | | | |
|---|---|---|---|
| 4,326,532 | 4/1982 | Hammar | 514/2 |
| 4,363,801 | 12/1982 | Nagyvary | 514/55 |
| 4,424,346 | 1/1984 | Hall et al. | 536/20 |
| 4,474,769 | 10/1984 | Smith | 536/20 |
| 4,626,287 | 12/1986 | Shah et al. | 514/892 |
| 4,671,823 | 6/1987 | Shah et al. | 514/892 |

FOREIGN PATENT DOCUMENTS 54-11955 1/1979 Japan ...................................... 536/20

*Primary Examiner*—Ronald W. Griffin
*Assistant Examiner*—Nancy S. Carson
*Attorney, Agent, or Firm*—Arnold, White & Durkee

[57] ABSTRACT

Methylated chitosans are used for the preparation of pharmaceutical compositions having improved laxative properties over commonly used laxative.

Said products are advantageouisly employed also in the preparation of ophtalmic solutions.

7 Claims, No Drawings

METHYLATED CHITOSANS AND THEIR USE FOR THE PREPARATION OF PHARMACEUTICAL COMPOSITIONS

The present invention relates to the use of methylated chitosans for the preparation of pharmaceutical compositions, in particular compositions useful as laxatives and as opthalmic solutions.

Methylated chitosans include N-dimethylchitosan and O-methyl-N-dimethyl chitosan with a number of methyl groups bound to oxygen comprised between 0.2 and 1.

The laxative mostly used for treating chronic constipation is methylcellulose, which when administered in a quantity of 1-1.5 g in one or two glasses of water forms a colloidal solution in the upper digestive tract and loses water in the colon to form a gel which increase the mass and reduces the consistency of the feces.

This very large water quantity is required because of the capacity of methylcellulose to swell and form compact masses which can cause esophageal and/or tracheal obstruction.

These risks remain in spite of the considerable dilution under which it is administered. Side effects have also been noted in the form of gastric disturbaces of dyspeptic type with a sensation of fullness and epigastric swelling.

We have now found that the drawbacks of methylcellulose are obviated by using methylated chitosans in the form of a concentrated solution which remains liquid in the esophageal gastric tract to gradually transform in the intestine into a fluid gel which performs its laxative function without involving any risk. N-alkylchitosans are known products which have been used up to the present time for preparing films and membranes able to absorb metal ions or products for use in chromatography (S. Hirano et al., Carbohydrate Research 71, 344 (1979); R. A. A. Muzzarelli et al., Carbohydrate Polymers 5, 297 (1985)).

In the known art, N-dialkylchitosans are prepared by alkylating chitosan in four stages: in the first stage, chitosan is reacted with formaldehyde in the presence of acetic acid in accordance with the reaction:

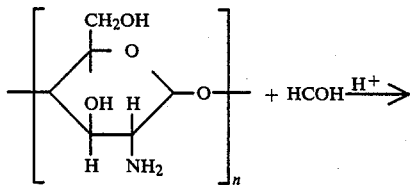

The product obtained is reduced with sodium borohydride to form N-monomethylchitosan in accordance with the reaction:

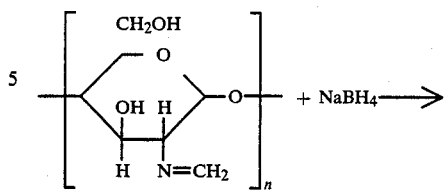

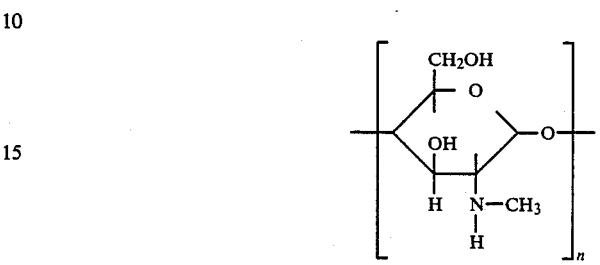

By further treating the N-monomethylchitosan with formaldehyde in acid followed by reduction with sodium hydroboride, N-dimethylchitosan is formed.

In addition to the drawback of its implementation in four stages, the described process also has the disadvantage of producing a final product which is not completely methylated.

Another process is known according to which chitosan is reacted in a single stage with formaldehyde in the presence of formic acid, which acts as a reaction solvent and reducing agent. The reaction involved in the process is as follows:

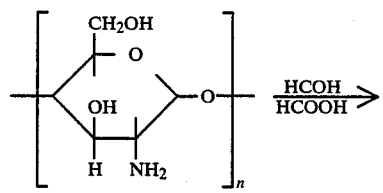

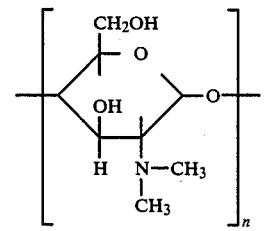

The preferred conditions for preparing N-dimethylchitosan useful in the preparation of pharmaceutical compositions according to the present invention are as follows: chitosan is dissolved in an aqueous formic acid solution in such a quantity as to obtain a solution of concentration between 10 and 200 g/l of chitosan and preferably between 50 and 150 g/l of chitosan.

Formaldehyde is added to said solution in such a quantity as to obtain a molecular ratio of formaldehyde to chitosan of between 2 and 10. The formic acid concentration is increased to between 0.2 and 0.5N, the temperature is raised to 40°-90° C., preferably to 80°-90° C., and the reaction is conducted for a time of between 4 and 24 hours.

The product obtained from the reaction is recovered and totally purified by precipitation in ethanol an/or acetone. Each gram of N-dimethylchitosan is able to retain from 25 to 35 g of water, and the volume of 1 g of dry gel after being brought to equilibrium with water at ambient temperature is 35-45 ml, according to the preparation conditions.

The intrinsic viscosity of the product, determined in 0.1M acetic acid and 0.1M sodium chloride at 25° C., is a 3.5-4/5 dl/g. For the preparation of O-methyl-N-dimethylchitosan, one starts from N-dimethylchitosan or directly from chitosan, using an alkylating agent such as methyl chloride or dimethyl sulphate. In the first case one operates as follows:

N-dimethylchitosan is treated at a temperature of 4°-15° C. with a 40% sodium hydroxide solution with a N-dimethylchitosan:NaOH ratio of between 1:07 and 1:1.5 and a water:N-dimethylchitosan ratio of between 1:1 and 1:05. The reaction is carried out in suitable reaction vessels in a nitrogen steam for 12 to 24 hours. The addition compound is submitted to methylation.

The methylation reaction is carried out in a autoclave under stirring with a methylchloride/N-dimethylchitosan 1:1 ratio at a temperature of 80°-110° C., under a pressure of 2 to 10 kg/cm$^2$, for 2 to 16 hours. The reaction product is washed with methanol and dried in air. The ratio of substitution (DS) of the hydroxy groups may vary between 0.2 and 1.0, the intrinsic viscosity of the product was found to be comprised between 1.5 and 2.5 dl/g.

In the second case one proceeds as follows: the reaction between chitosan and sodium hydroxide is carried out with a chitosan:NaOH ratio of between 1:1 and 1:3, at the temperature and for the duration employed in the methylation of N-dimethylchitosan. At the end the product is filtered out, suspended in methanol and methylated under stirring in a autoclave with a chitosan:methyl chloride ratio of 2:1, for 2 to 24 hours, under a pressure of 2 to 10 kg/cm$^2$.

The reaction product is washed with methanol and dried in air. At the $^{13}$C-NMR analysis the product is found to be completely dimethylated at the nitrogen and partially (0.2-0.5) substituted at the oxygen. The intrinsic viscosity was found to be comprised between 1.5 and 3 dl/g.

Further according to the present invention, we have also found that methylated chitosans can be used advantageously as laxative in chronic constipation. They form in fact a viscous solution at stomach pH (1.5-3.0) and forms gels of xerogel type at intestinal pH (6.5-7.3). Said products can also be used advantageously as opthalmic solutions.

The pharmacological characteristics of methylated chitosans are illustrated hereinafter by a description of the trials carried out by us on the toxicological aspect, the laxative effect and the applications in clinical oculistics.

Toxicological trials

The LD of methylated chitosans on oral administration was found greater than 4 g/kg both in rats of Sprague-Dawley stock and in mice of Swiss stock of both sexes.

Oral administration extended in time (6 months) in both Sprague-Dowley rats and Beagle dogs showed that at a dose of 2 g/kg/day no side effects are observed in the two types of animal treated. A rabbit's eye was treated with a solution prepared at a concentration of 0.5% for opthalmic use, for a period of three months at a dose of a few drops six times per day.

Even after three months no conjunctival and/or corneal irritative phenomena had appeared.

Tests on the laxative effect

In order to determine the laxative effect of methylated chitosans patients suffering from chronic constipation and using bulk-forming laxatives for regular evacuation were treated. Our case studies comprised 80 patients of between 36 and 71 years old who had already been under treatment for chronic constipation for at least six months. After a period of three weeks during which all treatment was suspended, a random division of the cases was made into four groups A, B, C and D each of 20 patients.

During this period the parameters recorded for quantifying the constipation were: (1) the number of weekly evacuations, (2) the consistency of the feces expressed by a semi-quantitative points system in which 1 corresponds to feces of normal consistency and 2 to feces of increased consistency, (3) intestinal pain, (4) anal pain pre and post evacuation, (5) loss of blood pre and post evacuation (Table 1). In evaluating the pain and blood loss, 1 point was allotted each time the symptom appeared, and Table 1 shows the sum of these points for each week of observation.

TABLE 1

| | | Laxative effect of methylated chitosans | | | | | | | | | | |
|---|---|---|---|---|---|---|---|---|---|---|---|---|
| | | NO TREATMENT | | | | | | | | | | |
| | | 1st week | | | | 2nd week | | | | 3rd week | | |
| PARAMETER | | A | B | C | D | A | B | C | D | A | B | C | D |
| No. of weekly | M | 1.22 | 1.18 | 1.25 | 1.23 | 0.08 | 0.96 | 1.06 | 0.98 | 0.80 | 0.84 | 0.91 | 0.86 |
| evacuations | SD | 0.74 | 0.65 | 0.69 | 0.66 | 0.51 | 0.48 | 0.51 | 0.50 | 0.42 | 0.47 | 0.48 | 0.46 |
| Consistency of | M | 1.80 | 1.84 | 1.74 | 1.76 | 1.84 | 1.88 | 1.77 | 1.82 | 1.88 | 1.87 | 1.80 | 1.85 |
| feces | SD | 0.51 | 0.52 | 0.56 | 0.55 | 0.45 | 0.50 | 0.54 | 0.52 | 0.54 | 0.53 | 0.58 | 0.55 |
| Pain pre and/or post-evacuation | M | 24 | 21 | 19 | 22 | 27 | 24 | 25 | 23 | 31 | 29 | 25 | 30 |
| Blood loss pre and/or post evacuation | M | 11 | 13 | 12 | 11 | 14 | 12 | 13 | 13 | 18 | 15 | 14 | 16 |
| Intestinal pain | M | 29 | 30 | 25 | 30 | 31 | 35 | 27 | 30 | 35 | 38 | 29 | 30 |
| | | TREATMENT | | | | | | | | | | |
| | | 1st week | | | | 2nd week | | | | 3rd week | | |
| | | A | B | C | D | A | B | C | D | A | B | C | D |
| No. of weekly | M | 2.2 | 2.7 | 1.19 | 3.6* | 3.4** | 3.5** | 1.36 | 4.2* | 3.6** | 3.8** | 1.74 | 4.6 |
| evacuations | SD | 0.86 | 0.94 | 0.66 | 1.18 | 1.26 | 1.24 | 0.82 | 1.29 | 1.40 | 1.36 | 0.93 | 1.32 |
| Consistency of | M | 1.51 | 1.43 | 1.69 | 1.14* | 1.29* | 1.30* | 1.65 | 1.10* | 1.14* | 1.12* | 1.62 | 1.08 |
| feces | SD | 0.29 | 0.31 | 0.45 | 0.21 | 0.23 | 0.26 | 0.46 | 0.14 | 0.17 | 0.13 | 0.42 | 0.07 |
| Pain pre and/or | M | 14 | 12 | 20 | 5 | 6* | 8* | 18 | 1 | 4** | 3** | 18 | 1 |

TABLE 1-continued

| | | | | | Laxative effect of methylated chitosans | | | | | | | | |
|---|---|---|---|---|---|---|---|---|---|---|---|---|---|
| post-evacuation | | | | | | | | | | | | | |
| Blood loss pre and/ or post-evacuation | M | 9 | 7 | 9 | 1 | 3 | 4 | 7 | 0 | 2* | 1* | 8 | 0 |
| Intestinal pain | M | 17 | 20 | 22 | 8 | 12 | 10* | 20 | 3 | 5* | 7* | 17 | 2 |

M = mean value;
SD = standard deviation
*P <0.05 with respect to values of A and B towards C in the same week of treatment
**P <0.01 with respect to values of A and B towards C in the same week of treatment After this period, the first group (A) was administered with 1 g+1 g per day of N-dimethylchitosan, prepared as described in Example 1, in sachets to form an extemporaneous solution, the second group (B) was administered with N-dimethylchitosan in 0.5 g tablets at a dose of 2+2 tablets per day, and the third group (C) was administered with methylcellulose in a quantity of 3 tablets (of 0.5 g) three times per day; the fourth group (D) was administered with O-methyl-N-dimethylchitosan, prepared as described in Example 2 and in the same way and dosage as for group B.

The treatment was continued for three weeks without dose variation by all patients, and all the previously considered parameters were recorded.

In order to evaluate the significance of the differences found in the parameters at the various times, the Student t test was used on the "No. of evacuations", and the X test was used on the other parameters.

From an examination of the results (Table 1) it is apparent that administering methylated chitosans enabled the abdomen of patients suffering from constipation to be regularised within a time of 1–2 weeks. Compared with the untreated groups of patients, a considerable increase in the number of weekly evacuations can be particularly noted, accompanied by normalisation of the feces consistency and almost total absence of abdominal and proctorrhea pain.

The administration of methylcellulose also improved constipation, but in a much less evident manner, and in this respect there is a statistically significant difference in the various parameters considered between the results obtained with methylated chitosans and with methylcellulose.

It should also be noted that no side effects either at the gastric or intestinal level appeared in any of the patients treated with methylated chitosans, and that the extemporaneous solution is easily swallowed and very palatable, and the tablets do not undergo any immediate swelling in the presence of aqueous solutions which could make them difficult to swallow.

In contrast, 5 patients who took methylcellulose complained of numerous episodes of epigastric swelling and dyspepsia.

Clinical oculistics tests

In order to check the "artificial tears" effect, 9 patients (4 women and 5 men) suffering from Sjogrens syndrome with keratoconjunctivitis sicca were treated with an aqueous solution of N-dimethylchitosan prepared as described in Example 1 or of O-methyl-N-dimethylchitosan prepared as described in Example 2, at a concentration of 0.2% and 0.5%, and with 1% methylcellulose.

Both the 0.2% solution and the 0.15% solution were used for 10 days, the patient being free to choose the number of administrations during the day.

Similar alleviation of ocular symptoms for the two concentrations was noted, with no side effects during treatment.

The administration of methylcellulose in a 1% aqueous solution was not able to improve the symptoms in the same manner, in that the patients had to increase the number of administrations, and the "dry eye" sensation did not completely disappear during the day. In conclusion, methylated chitosans prove to be products of considerable laxative effect without side effects, and with a greater effectiveness than an equal weight of methylcellulose.

In addition, they have excellent palatability when packed in sachets which when dissolved form a stable, easily swallowed medium-viscosity solution with the classical pH of the most acceptable drinks. Tablet administration produces no unpleasant sensation at the gastric level, and in particular there is no pyrosis, sense of swelling, hiccup, belching and/or reduction in appetite.

The ocular solution is even at a concentration of 0.2% able to soothe ocular symptoms in terms of reduction and loss of lacrimal secretion, its therapeutic effect being obtained at a lower concentration than methylcellulose and being longer lasting.

The following examples of the preparation of methylated chitosans are given for non-limitative illustration of the invention.

EXAMPLE 1

10 g of chitosan are dissolved in 100 ml of an aqueous 0.1N formic acid solution. 7.0 g of formaldehyde are added to this solution followed by formic acid until a 0.3N solution is obtained. The temperature is raised to 85° C. and the reaction carried out at this temperature under agitation for 15 hours. On termination of the reaction, 11.5 g of N-dimethylchitosan were recovered, the product on elementary and $^1H$ and $^{13}C$—NMR spectroscopic analysis proving to be totally methylated. Its intrinsic viscosity was 2.85 dl/g.

EXAMPLE 2

To a solution of 40 g sodium hydroxide in 1000 water are added 100 g chitosan.

The mixture is kept at 10° C. under stirring for 15 hours in a nitrogen atmosphere.

At the end the product is filtered out, suspended in 2000 ml methane and treated in a autoclave with 50 g methylchloride at a temperature of 20° C. and a pressure of 5 bar for 2 hours.

At the end the methylated chitosan is filtered, washed with little methanol and dried in air at 60° C.; 120 g of dry product are obtained. NMR analysis showed the product to be totally methylated at the nitrogen and partially (0.4 g methyl groups for each hydroxy group) at the oxygen.

The product had an intrinsic viscosity of 2.35 dl/g.

I claim:

1. A pharmaceutical composition for treatment of chronic constipation comprising a methylated chitosan selected from the group consisting of N-dimethylchitosan and O-methyl-N-dimethylchitosan which has a ratio of a number of methyl groups bound to oxygen to a number of available hydroxy groups between 0.2 and 1 in an amount effective against chronic constipation and a pharmaceutically acceptable carrier.

2. A method for treating chronic constipation which comprises orally administering to a patient suffering from constipation a methylated chitosan selected from the group consisting of N-dimethylchitosan and O-methyl-N-dimethylchitosan which has a ratio of a number of methyl groups bound to oxygen to a number of available hydroxy groups between 0.2 and 1 in an amount effective to produce a laxative effect.

3. The method of claim 2 wherein the amount of methylated chitosan administered is from 0.5 to 3 g/d.

4. The method of claim 2 wherein the methylated chitosan is administered in the form of solid tablets.

5. The method of claim 2 wherein the methylated chitosan is administered in the form of an aqueous solution.

6. A method for treating keratoconjunctivitis sicca which comprises topically administering to a patient suffering from keratoconjunctivitis sicca an aqueous solution containing from 0.1% to 0.5% of a methylated chitosan selected from the group consisting of N-dimethylchitosan and O-methyl-N-dimethyl-chitosan which has a ratio of a number of methyl groups bound to oxygen to a number of available hydroxy groups between 0.2 and 1 and an opthalmically acceptable carrier wherein the methylated chitosan is administered in an amount effective to alleviate said keratoconjunctivitis sicca.

7. An opthalmic composition for treatment of Keratoconjunctivitis sicca comprising a methylated chitosan selected from the group consisting of N-dimethylchitosan and O-methyl-N-dimethyl-chitosan which has a ratio of a number of methyl groups bound to oxygen to a number of available hydroxy groups between 0.2 and 1 in an amount effective against Keratoconjunctivitis sicca together with an ophthalmically acceptable carrier.

* * * * *